United States Patent [19]

Ward et al.

[11] Patent Number: 5,436,251
[45] Date of Patent: Jul. 25, 1995

[54] TREATMENT OF ANXIETY AND GASTROINTESTINAL DISORDERS WITH AZABICYCLO CARBONYL-2-(CYCLOPROPYLMETHYLOXY)BENZAMIDE

[75] Inventors: Terence J. Ward, Berks, England; Gerald Bradley, Perth, Australia

[73] Assignee: John Wyeth & Brother, Limited, Maidenhead, England

[21] Appl. No.: 106,461

[22] Filed: Aug. 13, 1993

[30] Foreign Application Priority Data

Aug. 19, 1992 [GB] United Kingdom ............ 9217629

[51] Int. Cl.⁶ ............................................. A61K 31/44
[52] U.S. Cl. ............................. 514/304; 514/214; 514/215; 546/124
[58] Field of Search ............... 514/214, 215, 304; 546/124

[56] References Cited

U.S. PATENT DOCUMENTS 4,983,600 1/1991 Ward et al. .................. 514/214

FOREIGN PATENT DOCUMENTS 2213816 8/1989 United Kingdom .
2236528 4/1991 United Kingdom .

Primary Examiner—Marianne M. Cintins
Assistant Examiner—T. J. Criares
Attorney, Agent, or Firm—Arthur G. Seifert

[57] ABSTRACT

(Endo)-N-[[[8-azabicyclo[3.2.1]octan-3-yl]amino]carbonyl]-2-(cyclopropylmethyloxy)benzamide and pharmaceutically acceptable salts thereof possess 5-HT$_3$ antagonistic activity and are useful in the treatment of neuro-psychiatric disorders (e.g. anxiety), gastro-intestinal disorders and migraine.

3 Claims, No Drawings

TREATMENT OF ANXIETY AND GASTROINTESTINAL DISORDERS WITH AZABICYCLO CARBONYL-2-(CYCLOPROPYLMETHYLOXY)-BENZAMIDE

This invention relates to aroyl urea derivatives.

GB 2213816A discloses a class of urea and carbamic acid derivatives, and the corresponding thio analogues of the general formula

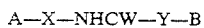
$$A-X-NHCW-Y-B \qquad (I)$$

In this formula, A represents an aromatic radical of the formula

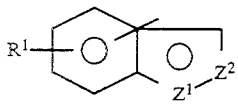
(a)

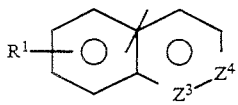
(b)

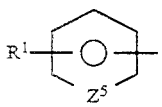
(c)

or

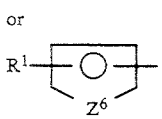
(d)

[where the free valence is attached to either fused ring of formula (a) or (b)]

$R^1$ represents hydrogen or one or more same or different substituents selected from lower alkyl, lower alkoxy, hydroxy, halogen, halo(lower)alkyl, amino, nitro, carboxamido, phenyl(lower)alkyloxy (in which the phenyl group may be optionally substituted by one or more lower alkyl, loweralkyloxy or halo substituents), (lower)alkylamino, di(lower)alkylamino or acylamino.

$Z^1$-$Z^2$ represents $CH_2$—CH, $NR^2$—CH, O—CH, S—CH, $CH_2$—N, O—N, S—N, $NR^2$—N, CH—$NR^2$ or N—$NR^2$, [where $R^2$ is hydrogen, (lower)alkyl or phenyl or phenyl(lower)alkyl in which the phenyl groups may optionally be substituted by one or more lower alkyl, lower alkyloxy or halo substituents]

$Z^3$-$Z^4$ represents CH=CH, O—$CH_2$ or N=CH $Z^5$ represents N or CH $Z^6$ represents O, S or NH X represents a direct bond or CO, W represents oxygen or sulphur, Y represents NH or O, B represents a saturated azacyclic ring of the formula

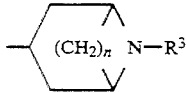
(II)

where n is 2, 3 or 4 and R is hydrogen, or (lower)alkyl, or

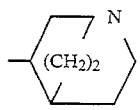
(III)

or the N-oxide thereof
or

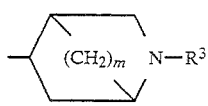
(IV)

where m is 1, 2 or 3 and R has the meaning given above
or

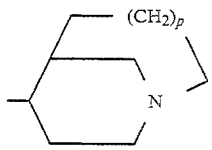
(V)

where p is 0, 1 or 2 or

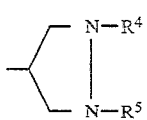
(VI)

where $R^4$ and $R^5$ are each hydrogen or lower alkyl with the proviso that when X is a direct bond, A represents a group of formula (c) or (d) and W represents oxygen, then the ring (c) or (d) does not contain a substituent ortho to the —X—NHCW—Y—B side chain.

The compounds disclosed in GB 2213816A are stated to possess pharmacological activity. In particular they are stated to antagonise 5-$HT_3$ receptors in warm blooded animals and hence be of value in conditions where antagonism of 5-$HT_3$ receptors is desirable. A particular use of 5-$HT_3$-antagonists is as anxiolytics.

A specific compound that falls within the general formula given above, but is not specifically disclosed in GB 2213816A, and its pharmaceutically acceptable salts are disclosed in GB 2236528A. The compounds are (endo)-N-[[(8-methyl-8-azabicyclo[3.2.1]octan-3-yl)amino]carbonyl]-2-(cyclopropylmethoxy]benzamide and its pharmaceutically acceptable acid addition salts. The free base has the formula:

(VII)
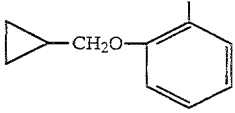

These compounds are stated to be more potent as 5-HT$_3$-antagonists and specifically as potential anxiolytics in pharmacological test procedures than the other members of the class of compounds of formula (I) disclosed in GB 2213816A.

GB 2236528A discloses that, the compound of formula (VII) may be prepared by inter alia methylating a compound of formula

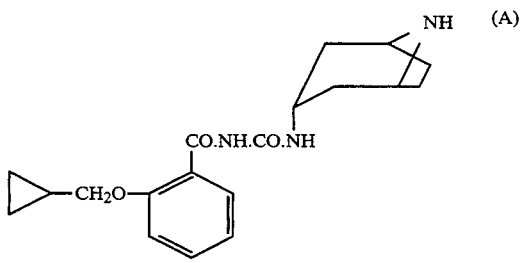

This compound is (endo)-N-[[[8-azabicyclo[3.2.1]-octan-3-yl]amino]carbonyl]-2-(cyclopropylmethyloxy)-benzamide (hereinafter referred to as 'Compound A').

We have now found that Compound A and its pharmaceutically acceptable acid addition salts possess 5-HT$_3$ antagonistic activity and are surprisingly more potent as 5-HT$_3$-antagonists and specifically as potential anxiolytics in pharmacological test procedures than both the compound of GB 2236528A and also the other members of the class of compounds of formula (I) disclosed in GB 2213816A.

Accordingly the present invention provides Compound A or a pharmaceutically acceptable acid addition salt thereof for use as a pharmaceutical, particularly for use as a 5-HT$_3$ antagonist (e.g. for use in antagonising 5-HT$_3$ receptors in a mammal, particularly a human) and more particularly for use as an anxiolytic.

5-HT$_3$ antagonists may be useful in the treatment of neuro-psychiatric disorders such as anxiety, psychotic disorders (e.g. schizophrenia), dependancy on drugs or other substances of abuse, cognitive disorders; in the treatment of gastro-intestinal disorders such as emesis and nausea and in the treatment of migraine. Accordingly compound A or a pharmaceutically acceptable salt thereof may be used in one or more of the above mentioned treatments.

For certain of the above mentioned conditions it is clear that the compounds may be used prophylactically as well as for the alleviation of acute symptoms. References herein to "treatment" or the Like are to be understood to include such prophylactic treatment, as well as treatment of the acute conditions.

The compounds of the invention are particularly indicated for the treatment of anxiety.

In another aspect the present invention provides a pharmaceutical composition comprising Compound A or a pharmaceutically acceptable acid addition salt thereof in association with a pharmaceutically acceptable carrier. The pharmaceutical composition may be used, for example, for treating conditions susceptible to treatment by a 5-HT$_3$ antagonist, such as those mentioned above particularly anxiety.

In a further aspect, the present invention provides a method for treating conditions susceptible to treatment by a 5-HT$_3$ antagonist, particularly anxiety or any of the other conditions mentioned above, in a mammal which comprises administering to said mammal an effective amount of Compound A or a pharmaceutically acceptable acid addition salt thereof.

Compound A, the compound of GB 2236528A and the compounds disclosed in GB 2213816A are tested for 5-HT$_3$ antagonistic activity in the rat vagus by the following procedure:

The method is similar to that described by Ireland and Tyers, Br. J. Pharmac., 1987, 90, 229–238 and is dependent upon the ability of 5-HT to depolarize the vagus nerve in vitro.

Segments of the vagus nerve from Sprague-Dawley rats were placed in a perspex chamber and perfused with Krebs solution. Electrodes, positioned at either end of the nerve segment, were used to record the potential differences which ensued upon the addition of various concentrations of 5-HT to one end of the nerve segment.

Concentration-response curves to 5-HT were obtained in this manner prior to and following equilibration of the nerve segment with Krebs solution containing the test-substance. A Schild analysis was performed on these results in order to obtain a measure of antagonist potency, expressed as a pA$_2$ value.

Results are given in the table below:

TABLE I

| Compound | pA$_2$ |
|---|---|
| Compound A | 9.4 |
| Compound of GB 2236528A | 8.9 |
| Compounds of GB 2213816A | |
| Example 1 | 8.5 |
| 2 | 6.7 |
| 5 | 8.0 |
| 7 | 7.9 |
| 12 | 8.5 |
| 13 | 7.4 |
| 14 | <6.5 |
| 15 | <6.5 |
| 16 | <6.5 |
| 17 | <6.5 |
| 18 | <6.5 |
| 19 | 6.9 |
| 20 | <6.5 |
| 21 | 8.35 |
| 22 | 8.7 |
| 23 | 7.8 |
| 24 | <6.5 |
| 25 | 8.6 |
| 26 | 6.6 |
| 27 | 8.1 |
| 28 | 7.25 |
| 29 | 8.15 |
| 30 | 7.6 |

The table shows that the compound of the invention is considerably more potent than all the other compounds, Compound A, the compound of GB 2236528A and a representative number of compounds disclosed in GB 2213816A which had high pA$_2$ values in the 5-HT$_3$-antagonist test procedure given above were tested for potential anxiolytic activity by a test procedure measuring mouse exploratory activity in a two-compartment light/dark box based upon the procedure of B Costall et al, Neuropharmacology, 1987, 26, 195–200 and J. N. Crawley et al, Pharmac. Biochemo Behav., 1980, 13, 167–170. The test involves observing groups of mice placed in an open topped box, one third of which is painted black and illuminated under a dim red light and partitioned from the remainder of the box which is painted white and brightly illuminated. Access between the two sections is via an opening in the centre of the partition. The groups of mice are treated with vehicle or test compound and various behavioural parameters of the animals are measured including the number of exploratory rearings made by the mice in each section and the number of times the mice cross lines marked on the floor of each section. For each treatment group the mean numbers of line crossings and rears in each section of the box are calculated. Differences between drug-treated groups and vehicle-treated controls are compared using Student's unpaired t-test. Standard anxiolytic agents significantly increase locomotion and rearing in the light section. Test compounds are considered to be active if they induce a similar set of changes and, in particular, if they produce a significant ($p<0.05$) increase in rearing activity in the light section of the box.

The minimum effective dose (MED) in mg/kg is given in Table B below:

TABLE II

| Compound | MED, mg/kg s.c. |
| --- | --- |
| Compound A | 0.001 |
| Compound of GB 2236528A | 0.01 |
| Compounds of GB 2213816A | |
| Example 1 | 0.1 |
| 5 | 0.1 |
| 13 | 1 |
| 21 | 1 |
| 22 | 1 |
| 25 | 1 |

The compound of the invention is clearly more potent than the other compounds in the table.

Compound A and the pharmaceutically acceptable salts thereof may be prepared by methods known in the art, for example methods disclosed in GB 2213816A and GB 2236528A.

A particularly preferred method of preparing compound A comprises demethylation or debenzylation of a compound of formula (VIII)

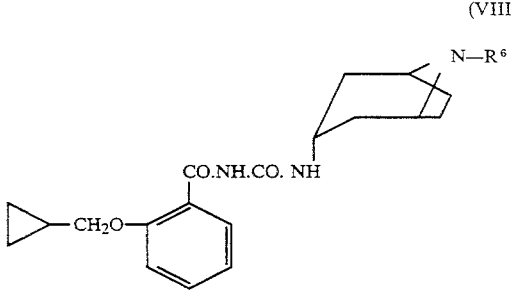

where $R^6$ is methyl or benzyl. The demethylation may be carried out, for example, with cyanogen bromide or with a chloroformate derivative (e.g. as described by J. H. Cooley and E. J. Evain, Synthesis, 1989, 1–7). Preferably the chloroformate derivative is 2,2,2-trichloroethyl chloroformate or more preferably α-chloroethyl chloroformate. The debenzylation can be carried out by catalytic hydrogenation (e.g. over palladium).

In an alternative method of preparing compound A 2-cyclopropylmethoxybenzoylurea is reacted with (endo)-8-azabicyclo[3.2.1]octan-3-amine. Preferably the reaction is carried out by heating the reactants, e.g. at reflux temperature, in an inert solvent.

Another method of preparing the compound of the invention comprises cyclopropylmethylating (endo)-N-[[(8-azabicyclo[3.2.1]octan-3-yl)amino]carbonyl]-2-hydroxybenzamide. The cyclopropylmethylation can be carried out with, for example, a cyclopropylmethyl halide (e.g. cyclopropylmethyl bromide) in presence of a base (e.g. KOH).

The compound of the invention may also be prepared by reacting cyclopropylmethanol with a compound of formula

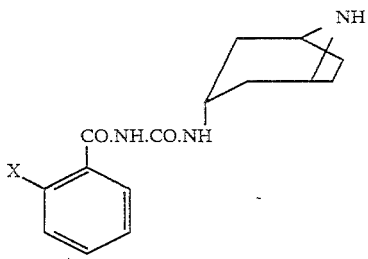

where X is a leaving group such as halogen (e.g. fluorine or chlorine) or an alkyl or aryl-sulphonyloxy group. The reaction can be carried out in the presence of a strong base (e.g. potassium tertiary butoxide) in, for example, a dipolar aprotic solvent.

The starting materials for the processes described above are described in the literature or may be prepared by known processes. Some of these processes are described, for example in GB 2213816A and 2236528A.

If in the process described above the compound is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

A pharmaceutical composition according to the invention comprises Compound A or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredients, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

The compounds of the invention can also be administered by the nasal route. When formulated for nasal administration the compositions may comprise a compound of the invention in a liquid carrier; such compositions may be administered for example in the form of a spray or as drops. The liquid carrier may be water (which may contain further components to provide the desired isotonicity and viscosity of the composition). The composition may also contain additional excipients such as preservatives, surface active agents and the like. The compositions may be contained in a nasal applicator that enables the composition to be administered as drops or as a spray. For administration from an aerosol container the composition should also include a propellant.

Pharmaceutical compositions for treatment and/or prevention of nausea or vomiting may contain a cyclo-oxygenase inhibitor in addition to a compound of the invention. Examples of cyclo-oxygenase inhibitors include systemic NSAID's e.g. indomethacin, piroxicam.

The antiemetic properties of the compounds of the invention are particularly advantageous in the treatment of nausea and vomiting associated with cancer chemotherapeutic agents and radiation therapy. The compounds are therefore of use in the treatment of cancer by chemotherapeutic agents (cytotoxic or cytostatic agents such as cisplatin, doxorubicin and cyclophosphamide) as well as irradiation. Accordingly the invention also provides a product containing a cancer chemotherapeutic agent and a compound of the invention as a combined preparation for simultaneous, separate or sequential use in cancer therapy.

Preferably the pharmaceutical composition is in unit dosage form, e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquids. The unit dosage form can be, for example, a capsule or tablet itself, or it can be-the appropriate number of any such compositions in package form.

The quantity of the active ingredient in unit dose of composition may be varied or adjusted from 0.5 mg or less to 750 mg or more, according to the particular need and the activity of the active ingredient.

The invention also includes the compounds in the absence of the carrier where the compounds are in unit dosage form.

The following Examples illustrate the invention.

EXAMPLE 1

(Endo)-N-E[[8-azabicyclo[3.2.1 1octan-3yl]amino]-carbonyl]-2-(cyclopropylmethyloxy)benzamide (Compound 2,2,2-Trichloroethyl chloroformate (2.3 g, 10.9 mmol) was added to a solution of (endo)-N-[[[8-methyl-8-azabicyclo[3.2.1]octan-3-yl]amino]carbonyl]-2-(cyclopropylmethyloxy)benzamide (3.58 g, 10 mmol) in 1,2-dichloroethane (50 ml) protected from moisture. The mixture was heated at reflux for 17 h. A further 0.5 ml of 2,2,2-trichloroethyl chloroformate was added and reflux continued for a further 6.5 h. The solution was cooled, washed with 2N hydrochloric acid, dried and evaporated. The residue was dissolved in glacial acetic acid (22.5 ml) and water (22.5 ml). Zinc powder (6 g) was added and the mixture stirred for 42 h. The mixture was filtered to remove unchanged zinc which was washed with methanol-acetic acid. The combined filtrate and washings were combined and evaporated. The residue was dissolved in dilute hydrochloric acid and washed with ether. The aqueous phase was basified to pH 10 with sodium hydroxide solution and shaken with chloroform. The mixture was filtered to remove zinc hydroxide and the chloroform separated from the aqueous phase. The aqueous phase was extracted further with chloroform and the chloroform extracts combined, dried (Na$_2$SO$_4$) and evaporated. The residue was dissolved in a mixture of methanol-ethyl acetate, acidified with sulphuric acid (0.2 ml) and concentrated with addition of further ethyl acetate to precipitate the bisulphate quarter hydrate (2.0 g) m.p. 177°–178° C. (dec).

EXAMPLE 2

(Endo)-N-[[[8-azabicyclo[3.2.1 1octan-3-yl]amino]carbonyl]-2-(cyclopropylmethyloxy)benzamide
(Compound A)

α-Chloroethyl chloroformate (1.43 g, 0.01 mol) was added dropwise over 15 min. to a stirred ice-cooled solution of (endo)-N-[[[8-methyl-8azabicyclo[3.2.1 ]octan-3-yl ]amino ]carbonyl ]-2(cyclopropylmethyloxy)-benzamide (1.785 g, 0.005 mol) in dichloromethane (100 ml) maintained below 5° C. The solution was stirred overnight, filtered and the fillrate evaporated. The residue was dissolved in ethanol (20 ml) and sulphuric acid (0.1 g) added followed by ether (10 ml) to precipitate the title compound as the bisulphate (1.3 g) m.p. 177°–178° C. (dec).

EXAMPLE 3

Preparation of Tablets

|  | Amount per tablet mg | | |
| --- | --- | --- | --- |
|  | (a) | (b) | (c) |
| Compound A | 1 | 5 | 10 |
| Microcrystalline cellulose | 49.25 | 47.25 | 44.75 |
| Modified food corn starch | 49.25 | 47.25 | 44.75 |
| Magnesium stearate | 0.5 | 0.5 | 0.5 |

Tablets are prepared from bulk amounts of ingredients in the proportions given above.

All of the compound A, cellulose and a portion of the corn starch are mixed and granulated to 10% corn starch paste. The resulting granulation is sieved, dried and blended with the remainder of the corn starch and the magnesium stearate. The resulting granulation is then compressed into tablets containing 1, 5 and 10 mg of the active ingredient per tablet.

EXAMPLE 4

Preparation of powder filled capsules

|  | Amount mg | |
| --- | --- | --- |
|  | (a) | (b) |
| Compound A | 10 | 15 |
| Avicel | 45 |  |
| Lactose | 153 |  |
| Starch (1500 NF) | — | 117 |
| Sodium starch glycollate | — | 6 |
| Magnesium stearate | 2 | 2 |

The formulations are prepared by admixing the ingredients in the proportions given above and filling two-part hard gelatin capsules with the required amount of the resulting mixture to give capsules containing 10 or 15 mg of Compound A.

We claim:

1. A method of treating neuro-psychiatric disorders, gastro-intestinal disorders or migraine which comprises administering to a mammal in need thereof an effective amount of (endo)-N-[[[8-azabicyclo[3.2.1]octan-3-yl]amino]carbonyl]-2-(cyclopropylmethyloxy)benzamide or a pharmaceutically acceptable salt thereof.

2. A method of treating anxiety which comprises administering to a mammal in need thereof an effective amount of (endo)-N-[[[8-azabicyclo[3.2.1]octan-3-yl]amino]carbonyl]-2-(cyclopropylmethyloxy)benzamide or a pharmaceutically acceptable salt thereof.

3. A pharmaceutical composition useful in the treatment of neuro-psychiatric disorders, gastrointestinal disorders or migraine which comprises (endo)-N-[[[8-azabicyclo[3.2.1]octan-3 -yl]amino]carbonyl]-2-(cyclopropylmethyloxy)benzamide or a pharmaceutically acceptable salt thereof in association with a pharmaceutically acceptable carrier.

* * * * *